(12) United States Patent
Daniel et al.

(10) Patent No.: US 8,704,009 B2
(45) Date of Patent: Apr. 22, 2014

(54) PROCESS FOR HYDROGENATING ALKYL ESTER(S) IN THE PRESENCE OF CARBON MONOXIDE

(75) Inventors: Berian John Daniel, East Riding of Yorkshire (GB); Jon Michael Stewart Deeley, East Riding of Yorkshire (GB); Benjamin Patrick Gracey, East Riding of Yorkshire (GB); John Glenn Sunley, East Yorkshire (GB)

(73) Assignee: BP P.L.C., London (GB)

( * ) Notice: Subject to any disclaimer, the term of this patent is extended or adjusted under 35 U.S.C. 154(b) by 205 days.

(21) Appl. No.: 12/998,884

(22) PCT Filed: Dec. 10, 2009

(86) PCT No.: PCT/GB2009/002866
§ 371 (c)(1),
(2), (4) Date: Jul. 22, 2011

(87) PCT Pub. No.: WO2010/067079
PCT Pub. Date: Jun. 17, 2010

(65) Prior Publication Data
US 2011/0306805 A1    Dec. 15, 2011

(30) Foreign Application Priority Data

Dec. 12, 2008 (EP) ..................................... 08253988

(51) Int. Cl.
*C07C 29/149* (2006.01)

(52) U.S. Cl.
USPC ........................................................ 568/885

(58) Field of Classification Search
USPC ........................................................ 568/885
See application file for complete search history.

(56) References Cited

U.S. PATENT DOCUMENTS

| 3,326,956 A | 6/1967 | Davies et al. |
| 4,122,110 A | 10/1978 | Sugier et al. |
| 4,831,060 A | 5/1989 | Stevens et al. |
| 5,169,869 A | 12/1992 | Miller et al. |
| 2008/0194397 A1 | 8/2008 | Barnicki |
| 2008/0194398 A1 | 8/2008 | Barnicki |

FOREIGN PATENT DOCUMENTS

| CA | 1 159 435 A | 12/1983 |
| EP | 0 210 795 | 2/1987 |
| EP | 0 303 438 A2 | 2/1989 |
| GB | 2 150 560 | 7/1985 |
| WO | WO 83/03409 A1 | 10/1983 |
| WO | WO 99/02254 A1 | 1/1999 |
| WO | WO 00/23689 A1 | 4/2000 |

OTHER PUBLICATIONS

International Search Report for PCT/GB2009/002866, mailed Mar. 29, 2010.
Written Opinion of the International Searching Authority for PCT/GB2009/002866, mailed Mar. 29, 2010.
International Preliminary Report on Patentability for PCT/GB2009/002866, dated Oct. 6, 2010.
Elliott, D.J., et al; "Mechanism of Ethanol Formation from Synthesis Gas over CuO/ZnO/Al$_2$O$_3$"; *Journal of Catalysis*, vol. 114, pp. 90-99 (1988).
"Selection of Technology for Large Methanol Plants" by Helge Holm-Larsen, presented at the 1994 World Methanol Conference, Nov. 30-Dec. 1, 1994 in Geneva, Switzerland.
Gunardson, H.H., et al; "Produce CO-rich synthesis gas"; *Hydrocarbon Processing*, vol. 78, No. 4, pp. 87-90 and 92-93 (1999).
Bourbonneux, G.; "Fisher-Tropsch synthesis gas production routes"; *Petrole et Techniques;* vol. 415, pp. 86-93 (1998).
Mayer, J., et al; "A Microstructured Reactor for the Catalytic Partial Oxidation of Methane to Syngas"; *IMRET 3: Proceedings of the Third International Conference on Microreaction Technology*, ed. W. Ehrfeld, Springer Verlag, pp. 187-196 (1999).
Linthwaite, M., et al; "Compact retormers in gas conversion"; *Hydrocarbon Engineering*, vol. 5, No. 5, pp. 67-69 (2000).
*Hydrocarbon Processing*, vol. 79, No. 9, p. 34 (2000).
*Today's Refinery*, vol. 15, No. 8, p. 9 (2000).
*Today's Refinery*, vol. 15, No. 8, p. 9 (2000).

*Primary Examiner* — Elvis O Price
(74) *Attorney, Agent, or Firm* — Nixon & Vanderhye P.C.

(57) ABSTRACT

Process for the preparation of alcohol(s) from alkyl ester(s) by bringing hydrogen, carbon monoxide and at least one alkyl ester into contact with a hydrogenation catalyst including copper and manganese in a reaction zone to produce at least one alcohol. The molar ratio of hydrogen to carbon monoxide in the reaction zone is in the range of from 100:1 to 1:10.

14 Claims, No Drawings

PROCESS FOR HYDROGENATING ALKYL ESTER(S) IN THE PRESENCE OF CARBON MONOXIDE

This application is the U.S. national phase of International Application No. PCT/GB2009/002866, filed 10 Dec. 2009, which designated the U.S., and claims priority to EP Application No. 08253988.3, filed 12 Dec. 2008, the entire contents of each of which are hereby incorporated by reference.

The present invention relates to the preparation of alcohol(s) by the hydrogenation of alkyl ester(s). In particular, the present invention relates to a process for preparing alcohol(s) from alkyl ester(s) wherein hydrogen, carbon monoxide and at least one alkyl ester are brought into contact with a hydrogenation catalyst comprising copper and manganese.

In recent years increased use and demand for alcohols such as methanol, ethanol and higher alcohols has led to a greater interest in processes relating to alcohol production. Alcohols may be produced by the fermentation of, for example, sugars and/or cellulosic materials.

Other processes for the production of alcohols, in particular ethanol and higher alcohols, include the processes described hereinafter.

U.S. Pat. No. 4,122,110 relates to a process for manufacturing alcohols, particularly linear saturated primary alcohols, by reacting CO with $H_2$ at a pressure between 2 and 25 MPa and a temperature between 150 and 400° C., in the presence of a catalyst, characterized in that the catalyst contains at least 4 essential elements: (a) copper (b) cobalt (c) at least one element M selected from chromium, iron, vanadium and manganese, and (d) at least one alkali metal.

Journal of Catalysis, 1988, 114, 90-99 discloses a mechanism of ethanol formation from synthesis gas over $CuO/ZnO/Al_2O_3$. The formation of ethanol from CO and $H_2$ over a CuO/ZnO methanol catalyst (a hydrogenation catalyst) is studied in a fixed-bed microreactor by measuring the isotopic distribution of the carbon in the product ethanol when isotopically-enriched $^{13}C$ methanol was added to the feed.

US 2008/0194397 A1 discloses hydrogenation catalysts comprising copper chromite having ruthenium and one or more promoters deposited thereon, and the use of such catalysts for the preparation of methanol by the hydrogenation of carbon monoxide and for the preparation of alcohols by the hydrogenation of carbonyl compounds to alcohols.

US 2008/0194398 A1 US 2008/0194397 A1 discloses hydrogenation catalysts comprising copper chromite having palladium and lanthanum deposited thereon, and the use of such catalysts for the preparation of methanol by the hydrogenation of carbon monoxide and for the preparation of alcohols by the hydrogenation of carbonyl compounds to alcohols.

EP 0210795 A1 discloses the production of alcohols by the hydrogenation of carboxylic acid esters at elevated temperature and atmospheric or elevated pressure in the presence of a catalyst containing copper and at least one of magnesium, a lanthanide metal or an actinide metal.

GB 2150560 A discloses a process for the production of alcohols by hydrogenolysis of carboxylic acid esters, said process comprising contacting a vaporous mixture containing the ester, hydrogen and a minor amount of carbon dioxide, with a catalyst consisting essentially of a reduced mixture of copper oxide and zinc oxide at a temperature in the range of from about 150-240° C. and a pressure of from about 5-50 bar.

WO 8303409 describes a process whereby ethanol is produced via the carbonylation of methanol by reacting CO in the presence of a carbonylation catalyst to form ethanoic acid, where the ethanoic acid is then converted to an ethanoate ester, which is then hydrogenated to give ethanol or a mixture of ethanol and another alcohol which can be separated by distillation. Carbonylation can be effected using a $CO/H_2$ mixture and hydrogenolysis can similarly be conducted in the presence of CO, leading to the possibility of circulating gas between the carbonylation and hydrogenolysis zones with synthesis gas, preferably synthesis gas having a 2:1 $H_2$:CO molar ratio, being used as make up gas.

As the importance of alcohols, such as ethanol, is ever increasing in today's world, so is the need and desire to produce alcohols with a higher conversion rate, improved selectivity and improved productivity.

It has now surprisingly been found that when a hydrogenation catalyst comprising copper and manganese is used in the preparation of alcohol(s) from alkyl ester(s), the presence of carbon monoxide in the reaction zone can be beneficial in terms of improving the activity of the catalyst, increasing the rate of hydrogenation of the alkyl ester(s) and increasing the alcohol(s) productivity of the hydrogenation process.

The present invention provides a process for the preparation of alcohol(s) from alkyl ester(s) wherein hydrogen, carbon monoxide and at least one alkyl ester are brought into contact with a hydrogenation catalyst comprising copper and manganese in a reaction zone to produce at least one alcohol, wherein the molar ratio of hydrogen to carbon monoxide in the reaction zone is in the range of from 100:1 to 1:10.

The present invention further provides the use of carbon monoxide for increasing the catalytic activity of a hydrogenation catalyst comprising copper and manganese in a process for producing alcohol(s) from alkyl ester(s) and hydrogen.

The process for preparing alcohols provided by the present invention comprises contacting hydrogen ($H_2$), carbon monoxide (CO) and at least one alkyl ester with a hydrogenation catalyst comprising copper and manganese in a reaction zone.

The mechanism by which the alcohol(s) is prepared from the alkyl ester(s) is by the hydrogenation of the alkyl ester(s), i.e.

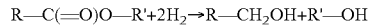

$$R-C(=O)O-R'+2H_2 \rightarrow R-CH_2OH+R'-OH$$

The hydrogenation of alkyl ester(s) to produce alcohols can also be referred to as the hydrogenolysis of alkyl ester(s).

Preferably, the at least one alkyl ester used in the process of the present invention is one or more alkyl ester having the formula R—C(=O)O—R', wherein R and R' are independently selected from aliphatic saturated hydrocarbons having from 1 to 5 carbon atoms, more preferably 1 to 3 carbon atoms, most preferably 1 or 2 carbon atoms. Preferred alkyl esters suitable for use in the process of the present invention are selected from methyl ethanoate, ethyl ethanoate, methyl propanoate, ethyl propanoate, propyl butanoate, butyl pentanoate and mixtures thereof. The most preferred alkyl esters for use in the process of the present invention are methyl ethanoate, ethyl ethanoate and mixtures thereof.

The source of the alkyl ester(s) used in the process of the present invention is not critical. According to an embodiment of the present invention, at least part of the alkyl ester(s) used in the process of the present invention are contained in an alkyl ester composition produced by an alcohol carbonylation reaction. When at least part of the alkyl ester(s) used in the process of the present invention are contained in an alkyl ester composition produced by an alcohol carbonylation reaction, said alkyl ester composition is preferably purified to remove carboxylic acids (for example ethanoic acid) and water before being introduced into the reaction zone. Therefore, in a preferred embodiment of the present invention, the alkyl ester(s) are contained in an alkyl ester composition which contains less than 5 wt. % carboxylic acids (relative to the amount of alkyl ester(s)), more preferably less than 1 wt. %, even more preferably less than 0.1 wt. % and most preferably less than 100 ppm by weight carboxylic acids. Said alkyl ester composition preferably contains less than 20 wt. % water (relative to the amount of alkyl ester(s)), more preferably less than 2 wt. %, and most preferably less than 0.2 wt. % water.

The source of the hydrogen ($H_2$) used in the process of the present invention is not critical. Non-limiting examples of processes which may provide a source of hydrogen that may be used in the process of the present invention include synthesis gas generation processes; the hydrolysis of water; and various other chemical processes, such as, for example, ethane crackers, styrene manufacture and catalytic reforming.

Conveniently, at least part of the hydrogen used in the process of the present invention can be derived from a synthesis gas generation process. Therefore, according to an embodiment of the present invention, at least part, preferably all, of the hydrogen used in the process of the present invention is derived from a synthesis gas generation process.

The source of the carbon monoxide (CO) used in the process of the present invention is not critical. Non-limiting examples of processes which may provide a source of carbon monoxide that may be used in the process of the present invention include synthesis gas generation processes; the reduction of metal oxides; and various other chemical processes, such as, for example, the high temperature reaction of air or oxygen with a carbonaceous material (for example coal).

Conveniently, at least part of the carbon monoxide used in the process of the present invention can be derived from a synthesis gas generation process. Therefore, according to an embodiment of the present invention, at least part, preferably all, of the carbon monoxide used in the process of the present invention is derived from a synthesis gas generation process.

Conveniently, in the process of the present invention, hydrogen, carbon monoxide and at least one alkyl ester can be introduced into a reaction zone, wherein within said reaction zone the hydrogen, carbon monoxide and at least one alkyl ester are brought into contact with a hydrogenation catalyst comprising copper and manganese to produce at least one alcohol product, the alcohol product can then be withdrawn from the reaction zone as an alcohol containing product stream.

According to a particular embodiment of the present invention, the hydrogen, carbon monoxide and at least one alkyl ester are introduced into a reaction zone containing a hydrogenation catalyst comprising copper and manganese in one or more feed streams. That is, the hydrogen, carbon monoxide and the at least one alkyl ester can be introduced into the reaction zone as one or more combined feed stream(s), separate feed streams, or any combination thereof. By the term "combined feed stream" it is meant a feed stream which contains at least part of two or more of the hydrogen, carbon monoxide component and the at least one alkyl ester components of the process of the present invention. By the term "separate feed stream" it is meant a feed stream which contains at least part of one of the hydrogen, carbon monoxide and the at least one alkyl ester components of the process of the present invention.

According to another particular embodiment of the present invention, at least one of the hydrogen, carbon monoxide or the at least one alkyl ester components of the process of the present invention is contained within a reaction zone prior to the introduction of the other components and/or the hydrogenation catalyst comprising copper and manganese. That is, the reaction zone may contain hydrogen, carbon monoxide and the at least one alkyl ester prior to the introduction of the hydrogenation catalyst comprising copper and manganese, or the reaction zone may contain the hydrogenation catalyst comprising copper and manganese and at least one of the components selected from hydrogen, carbon monoxide and the at least one alkyl ester prior to the introduction of the other component(s) selected from hydrogen, carbon monoxide and the at least one alkyl ester.

Advantageously, because the process of the present invention requires the presence of both hydrogen and carbon monoxide in the reaction zone, hydrogen and/or carbon monoxide sourced from synthesis gas can be used in the process of the present invention without the need to perform a process to separate hydrogen from carbon monoxide (for example by cryogenic separation). Therefore, according to an embodiment of the present invention, at least part, preferably all, of the carbon monoxide and at least part, preferably all, of the hydrogen used in the process of the present invention are sourced from a process generating synthesis gas.

When at least part of the hydrogen and/or carbon monoxide used in the process of the present invention is sourced from a synthesis gas generation process, the synthesis gas produced by the synthesis gas generation process may also be subjected to a process to remove carbon dioxide. Treatment of synthesis gas to remove carbon dioxide is well known in the art. Therefore, according to an embodiment of the present invention, the process of the present invention can be performed in the absence of carbon dioxide.

When a synthesis gas generation process is used to provide a source of hydrogen and/or carbon monoxide for the process of the present invention, the synthesis gas generation process used and the carbonaceous feedstock used in the synthesis gas generation process is not critical to the process of the present invention.

In one particular embodiment of the present invention, at least part of, preferably all of, the hydrogen and at least part of, preferably all of, the carbon monoxide are introduced into the reaction zone in the same feed stream. The hydrogen and carbon monoxide in said feed stream may be derived from the same synthesis gas generation process as a synthesis gas stream. Said synthesis gas stream may optionally have been treated to remove carbon dioxide.

The molar ratio of carbon monoxide to hydrogen in a synthesis gas stream produced by a synthesis gas generation process is dependent upon the process and feedstock used. Hydrogen content of synthesis gas can be increased by subjecting the synthesis gas to a water gas shift reaction.

In the process of the present invention, the molar ratio of hydrogen to carbon monoxide ($H_2$:CO) is in the range of from 100:1 to 1:10. Preferably the ratio of hydrogen to carbon monoxide ($H_2$:CO) in the reaction zone is at most 50:1, more preferably at most 25:1. Preferably the molar ratio of hydrogen to carbon monoxide ($H_2$:CO) in the reaction zone is at least 1:5, more preferably at least 1:2.

According to an embodiment of the present invention, carbon monoxide represents more than 1 mol %, preferably more than 10 mol % and most preferably more than 20 mol % of the total amount of hydrogen and carbon monoxide introduced to the reaction zone; and less than 90 mol %, preferably less than a 80 mol % and most preferably less than 50 mol % of the total amount of hydrogen and carbon monoxide introduced to the reaction zone.

Preferably, the molar ratio of hydrogen to alkyl ester(s) ($H_2$:alkyl ester(s)) in the process of the present invention is at least 1.5:1, more preferably at least 2:1 and most preferably at least 5:1. Preferably the molar ratio of hydrogen to alkyl ester(s) (H$_2$:alkyl ester(s)) in the reaction zone is at most 100:1, more preferably at most 50:1 and most preferably at most 15:1.

According to an embodiment of the present invention, the at least one alkyl ester represents more than 1 mol %, preferably more than 5 mol % and most preferably more than 10 mol % of the total amount of hydrogen and alkyl ester(s) introduced to the reaction zone; and less than 40 mol %, preferably less than a 30 mol % and most preferably less than 20 mol % of the total amount of hydrogen and alkyl ester(s) introduced to the reaction zone.

Other components, such as diluent gases (for example nitrogen) and/or inert solvents, may optionally be present in the reaction zone, or in any of the feeds introduced into the reaction zone.

The hydrogenation catalyst comprising copper and manganese is any catalyst known to be effective in the hydrogenation of alkyl esters to alcohols which contains copper and manganese. The hydrogenation catalyst comprising copper and manganese used in the hydrogenation of alkyl esters to alcohols are typically solid catalysts and may be supported on any known catalyst support material.

The hydrogenation catalyst comprising copper and manganese of the present invention comprises:
 (a) a copper component;
 (b) a manganese component; and preferably
 (c) at least one additional component selected from metal oxides, silicon oxide, clay, carbon and graphite.

Preferably, the copper component (a) is copper metal or copper oxide, more preferably copper oxide. Conveniently, the copper component of the hydrogenation catalyst comprising copper and manganese can be incorporated into the catalyst composition in a form that is readily converted to copper oxide or copper; for example, the copper component may conveniently be introduced into the catalyst composition as a copper salt, and the copper salt is then converted to copper oxide by subjecting the catalyst composition to appropriate conditions (e.g. the copper component may be introduced into the catalyst as copper (II) nitrate, which is then converted to copper oxide by thermal decomposition).

Preferably, the manganese component (b) is manganese metal or a manganese oxide, more preferably a manganese oxide. Conveniently, the manganese component of the hydrogenation catalyst comprising copper and manganese can be incorporated into the catalyst composition in a form that is readily converted to a manganese oxide or manganese; for example, the manganese component may conveniently be introduced into the catalyst composition as manganese salt, and the manganese salt is then converted to a manganese oxide (for example MnO or MnO$_2$) by subjecting the catalyst composition to appropriate conditions (e.g. the manganese component may be introduced as manganese (II) nitrate, which is then converted to a manganese oxide by thermal decomposition).

Preferably, component (c) is one or more metal oxide. Examples of metal oxides suitable for use in the additional component (c) include aluminium oxide, zirconium oxide, zinc oxide, chromium oxide, titanium oxide, magnesium oxide, calcium oxide, and mixtures thereof. Preferred metal oxides include zinc oxide, zirconium oxide and aluminium oxide.

The additional component (c) may conveniently be incorporated into the catalyst composition in admixture with the copper component (a) and the manganese component (b), or may be employed as a support material upon which the copper component (a) and manganese component (b) is deposited.

Therefore, according to an embodiment of the present invention, the hydrogenation catalyst comprising copper and manganese contains a copper component and a manganese component supported on a support material selected from metal oxides, silicon oxide, clay, carbon and graphite, and mixtures thereof; preferably, the copper component and the manganese component are supported on a support material selected from carbon, silica, titania, clays, alumina, zinc oxide, zirconia, and mixtures thereof; more preferably the copper component and the manganese component are supported on alumina.

Whilst not wishing to be bound by theory, it is believed that the copper component of the hydrogenation catalyst comprising copper and manganese is the catalytically active component and the manganese component of the hydrogenation catalyst comprising copper and manganese is a promoter to the catalytically active copper component. Therefore, the hydrogenation catalyst comprising copper and manganese preferably contains a catalytically effective amount of copper and a promoting amount of manganese.

In a preferred embodiment of the present invention, the hydrogenation catalyst comprising copper and manganese contains at least 5 wt. % copper based on the total weight of the catalyst, more preferably at least 10 wt. % copper, even more preferably at least 20 wt. % copper; and at most 80 wt. % copper, more preferably at most 60 wt. % copper and even more preferably at most 50 wt. % copper.

In a preferred embodiment of the present invention, the hydrogenation catalyst comprising copper and manganese contains at least 0.1 wt. % manganese based on the total weight of the catalyst, more preferably at least 1 wt. % manganese, even more preferably at least 2 wt. % manganese; and at most 50 wt. % manganese, more preferably at most 20 wt. % manganese and even more preferably at most 10 wt. % manganese.

In a preferred embodiment of the present invention, the hydrogenation catalyst comprising copper and manganese is a manganese-containing copper chromite catalyst or a mixed metal oxide catalyst containing copper oxide, manganese and at least one other metal oxide.

Copper chromite based hydrogenation catalysts are known in the art, for example in U.S. Pat. No. 5,169,869, US 2008/0194397 A1 and US 2008/0194398 A1, and any such known copper chromite based hydrogenation catalyst which contain manganese may be used in the process of the present invention.

Copper chromite is generally charaterised as non-stoichiometric mixed copper-chromium oxides which are prepared by coprecipitation. Methods of preparing copper chromite catalysts by coprecipitation are known in the art.

Mixed metal oxide catalyst containing copper oxide, manganese and at least one other metal oxide are also known in the art, for example in GB 2150560 A and CA 1159435 A, and any such known mixed metal hydrogenation catalyst which contain manganese may be used in the process of the present invention.

If the hydrogenation catalyst comprising copper and manganese used in the present invention is a mixed metal oxide catalyst containing copper oxide, manganese and at least one other metal oxide, then preferably the catalyst comprises copper oxide, manganese oxide and a third component selected from aluminium oxide, zirconium oxide, zinc oxides, chromium oxides, titanium oxides, magnesium oxides, calcium oxides, and mixtures thereof. Preferably, the third component is selected from aluminium oxide, zinc oxide, zirconium oxide and mixtures thereof; more preferably the third component is selected from aluminium oxide, zinc oxide and mixtures thereof. A particularly preferred mixed metal oxide catalyst containing copper oxide, manganese and at least one other metal oxide is a mixed metal oxide catalyst containing copper oxide, manganese oxide and aluminium oxide.

Typically, before being employed in the process of the present invention, the hydrogenation catalyst comprising copper and manganese is activated. Activation of hydrogenation catalyst comprising copper and manganese is known in the art. Conveniently, activation of the catalyst can be performed by heating of the catalyst in a reducing atmosphere, such as heating the catalyst, preferably to a temperature of at least 180° C., more preferably at least 190° C., in a hydrogen containing atmosphere, such as a synthesis gas atmosphere, preferably an atmosphere containing at least 50 mol % hydrogen, more preferably at least 70 mol % hydrogen, most preferably 100 mol % hydrogen.

The hydrogenation process of the present invention may be operated in the gas phase, or a mixed gas/liquid phase. The mixed gas/liquid phase is where at least part of the alkyl ester to be hydrogenated is in the liquid phase. Preferably, the at least one alkyl ester that is brought into contact with the hydrogenation catalyst comprising copper and manganese in the reaction zone is in the gas phase. Therefore, according to an embodiment of the present invention, the at least one alkyl ester is vapourised before being introduced to the reaction zone.

The hydrogenation process of the present invention can be conducted in batch, semi continuous or continuous mode, with continuous mode of operation being preferred.

The hydrogenation reaction can be conducted in adiabatic or isothermal mode; wherein adiabatic mode of operation is preferred.

The process of the present invention is preferably operated at a temperature of at least 150° C.; preferably, the process of the present invention is also operated at a temperature of at most 290° C.

According to a preferred embodiment of the present invention, the hydrogenation reaction temperature is greater than 150° C., preferably at least 170° C. and most preferably at least 190° C.; and preferably at most 250° C., more preferably at most 230° C. and most preferably at most 220° C.

The process of the present invention is preferably operated at a pressure of at least 1 MPa, more preferably at a pressure of at least 3 MPa and most preferably at a pressure of at least 5 MPa. The process of the present invention is also preferably operated at a pressure of at most 15 MPa, more preferably at a pressure of at most 13 MPa and most preferably at a pressure of at most 9 MPa.

The GHSV (gas hourly space velocity) for continuous operation may be in the range 50 to 50,000 $h^{-1}$, preferably from 1,000 to 30,000 $h^{-1}$ and most preferably from 2,000 to 9,000 $h^{-1}$.

If the alkyl ester is introduced into the reaction zone as a liquid, the alkyl ester introduced into the reaction zone preferably has an LHSV (liquid hourly space velocity) of less than 10 $h^{-1}$, more preferably less than 5 $h^{-1}$ and most preferably less than 3 $h^{-1}$; for example, a typical LHSV for normal operation is approximately 1 $h^{-1}$.

For the purposes of calculating the GHSV and/or the LHSV of the present invention, when multiple reactors are used, said "catalyst volume" refers to the combined volume of the catalyst in all the reactors.

The reaction zone of the present invention can conveniently be any reactor, multiple reactors, such as a series of reactors, or a part thereof, wherein the process of the present invention occurs.

Suitable reactors which may be used in the process of the present invention include adiabatic bed, multi-tubular, fluidised bed, spinning basket and buss loop, and heat exchanger reactors. When more than one reactor is used, the reactors may be arranged either in series or in parallel. For reactors utilised in series, heat exchangers and/or intercoolers and/or additional reactant and/or recycle of intermediates can be employed in between successive reactors to control the reaction temperature. In one embodiment of the present invention, the process is performed in at least two adiabatic reactors in series.

The process of the present invention may also be performed in a conventional methanol synthesis reactor. When the process of the present invention is performed in a conventional methanol synthesis reactor, methanol can be co-produced in addition to the alcohols produced by the hydrogenation of the alkyl ester.

In addition to the production of alcohol(s), the hydrogenation process may also produce other reaction by-products, such as other alkyl ester(s) (arising through trans-esterification), and trace amounts of methane, ethane, water, ethers and aldehydes.

The alcohols produced in the process of the present invention are conveniently withdrawn from the reaction zone as an alcohol containing product stream. The alcohol containing product stream is then preferably subjected to a separation stage, whereby a fraction comprising the desired alcohol(s) is separated and recovered. The separated and recovered alcohol(s) may comprise a single alcohol or a mixture of alcohols, for example, the separated and recovered alcohol(s) may comprise methanol, ethanol, propanol(s) (n-propanol with low amounts of iso-propanol), butanol(s) (n-butanol and iso-butanol) and pentanol(s), and mixtures thereof.

According to a preferred embodiment of the present invention, an alcohol containing product stream is withdrawn from the reaction zone, said alcohol containing product stream is first subjected to a cooling stage, and then the cooled alcohol containing product stream is subjected to a separation phase, e.g. flash separation, where any low boiling components and remaining gaseous reactants are separated from an alcohol product composition. After this treatment, a gaseous stream containing the majority of the hydrogen, carbon monoxide and any other inert gases that may be present (including light alkanes; nitrogen; and $CO_2$) in the alcohol containing product stream is recovered. The recovered gaseous stream may then optionally be recycled to the reaction zone.

The present invention also provides the use of carbon monoxide for increasing the catalytic activity of a hydrogenation catalyst comprising copper and manganese in a process for producing alcohol(s) from alkyl ester(s) and hydrogen. By the term "a process for producing alcohol(s) from alkyl ester(s) and hydrogen", it is meant that the alcohol(s) are prepared by the hydrogenation of alkyl ester(s) as previously described herein. By the term increasing the catalytic activity of a hydrogenation catalyst comprising copper and manganese, it is meant that the overall rate of hydrogenation in the process for producing alcohol(s) from alkyl ester(s) and hydrogen is increased when carbon monoxide is present relative to the rate of hydrogenation in the absence of carbon monoxide.

The present invention yet further provides a method of increasing the rate of hydrogenation of a process for preparing alcohol(s) from alkyl ester(s), said method comprises bringing carbon monoxide in addition to hydrogen and at least one alkyl ester into contact with a hydrogenation catalyst comprising copper and manganese in a reaction zone.

It should be noted that whilst all of the aforementioned temperature and pressure operating conditions form preferred embodiments of the present invention, they are not, by any means, intended to be limiting, and the present invention hereby includes any other pressure and temperature operating conditions that achieve the same effect.

EXAMPLES

Catalysts

The catalysts used in the following examples were T-4489 (Süd-Chemie), which has the following composition: CuO (56 wt. %), $MnO_2$ (10 wt. %), $Al_2O_3$ (34 wt. %); and T-2130 (Süd-Chemie), which has the following composition: CuO (33 wt. %), ZnO (66 wt. %).

Catalyst Testing

The catalyst testing was carried out in parallel pressure flow reactors. The catalysts were heated to 100° C. under a flow of 5 mol % $H_2$ in $N_2$ at 2.5 MPa and a GHSV of 6000 $h^{-1}$. The concentration of $H_2$ was increased in stages to 10, 20, 40, 70 and 100 mol % with a 1 hour dwell time at each stage. The catalysts were then heated at a rate of 1° C./min to a holding temperature of 200° C., where the conditions were held for a dwell time of 1.5 hours. At this point catalyst activation was considered complete.

Examples 1 to 5 and Comparative Example A to G

In Examples 1 to 5, mixtures of CO, $H_2$, $N_2$ and methyl ethanoate were passed over the T-4489 catalyst. In comparative Example A, the T-4489 catalyst was tested in the absence of CO. In comparative Examples C to G, mixtures of CO, $H_2$, $N_2$ and methyl ethanoate were passed over the T-2130 catalyst. In comparative Example B, the T-2130 catalyst was tested in the absence of CO. The products from each of the examples and comparative examples were detected and quantified by gas chromatography.

The conditions for each experiment are given in Table 1. Each Experiment lasted 24 hours.

The results from Examples 1 to 5 and comparative Examples A to G are presented in Table 2. It is clear from these results that the introduction of CO enhances the productivity of the hydrogenation catalyst containing copper and manganese (T-4489) and decreases the productivity of the non-manganese containing catalyst (T-2130).

TABLE 1

Feed compositions and reaction conditions for Examples 1-5 and comparative Examples A-G.

| Example | Temperature (° C.) | Pressure (bar) | GHSV ($h^{-1}$) | LHSV ($h^{-1}$) | $H_2$ (vol %) | CO (vol %) | AcOMe (vol %) | $N_2$ (vol %) |
|---|---|---|---|---|---|---|---|---|
| A* | 210 | 50.0 | 13473 | 2.4 | 47.45 | 0.00 | 4.90 | 47.60 |
| 1 | 210 | 50.0 | 13473 | 2.3 | 47.57 | 0.95 | 4.76 | 46.67 |
| 2 | 210 | 50.0 | 13473 | 2.3 | 47.57 | 4.76 | 4.76 | 42.86 |
| 3 | 210 | 50.0 | 13473 | 2.3 | 47.57 | 9.52 | 4.76 | 38.10 |
| 4 | 210 | 50.0 | 13473 | 2.3 | 47.57 | 28.57 | 4.76 | 19.05 |
| 5 | 210 | 50.0 | 13473 | 2.3 | 47.57 | 38.10 | 4.76 | 9.52 |
| B* | 210 | 50.0 | 13473 | 2.4 | 47.45 | 0.00 | 4.90 | 47.60 |
| C* | 210 | 50.0 | 13473 | 2.3 | 47.57 | 0.95 | 4.76 | 46.67 |
| D* | 210 | 50.0 | 13473 | 2.3 | 47.57 | 4.76 | 4.76 | 42.86 |
| E* | 210 | 50.0 | 13473 | 2.3 | 47.57 | 9.52 | 4.76 | 38.10 |
| F* | 210 | 50.0 | 13473 | 2.3 | 47.57 | 28.57 | 4.76 | 19.05 |
| G* | 210 | 50.0 | 13473 | 2.3 | 47.57 | 38.10 | 4.76 | 9.52 |

*Comparative
AcOMe—methyl ethanoate

TABLE 2

Results for Examples 1-5 and comparative Examples A-G.

| Example | Catalyst | AcOMe Conversion (%) | Productivity [g/(g · h)] | MeOH STY [g/(g · h)] | EtOH STY [g/(g · h)] | AcOEt STY [g/(g · h)] | Methane STY [g/(g · h)] | Ethane STY [g/(g · h)] |
|---|---|---|---|---|---|---|---|---|
| A* | T-4489 | 87.1 | 0.78 | 0.517 | 0.739 | 0.081 | 0.0014203 | 0.0003136 |
| 1 | T-4489 | 95.6 | 0.95 | 0.608 | 0.936 | 0.033 | 0.0016414 | 0.0007660 |
| 2 | T-4489 | 96.8 | 0.96 | 0.627 | 0.947 | 0.023 | 0.0017024 | 0.0015882 |
| 3 | T-4489 | 96.5 | 0.94 | 0.629 | 0.924 | 0.025 | 0.0017736 | 0.0017592 |
| 4 | T-4489 | 96.3 | 0.93 | 0.670 | 0.914 | 0.025 | 0.0018321 | 0.0014437 |
| 5 | T-4489 | 95.7 | 0.93 | 0.686 | 0.919 | 0.028 | 0.0018506 | 0.0012172 |
| B* | T-2130 | 56.1 | 0.53 | 0.406 | 0.411 | 0.221 | 0.0002400 | 0.0002040 |
| C* | T-2130 | 48.9 | 0.50 | 0.404 | 0.367 | 0.259 | 0.0002228 | 0.0001719 |
| D* | T-2130 | 38.6 | 0.39 | 0.341 | 0.256 | 0.264 | 0.0001746 | 0.0001128 |
| E* | T-2130 | 32.8 | 0.33 | 0.301 | 0.197 | 0.257 | 0.0001654 | 0.0000889 |
| F* | T-2130 | 25.3 | 0.25 | 0.248 | 0.128 | 0.239 | 0.0001479 | 0.0000000 |
| G* | T-2130 | 22.3 | 0.22 | 0.227 | 0.104 | 0.228 | 0.0001441 | 0.0000000 |

*Comparative
AcOMe—methyl ethanoate;
AcOEt—Ethyl Ethanoate;
MeOH—Methanol;
EtOH—Ethanol;
STY—Space Time Yield
Productivity = EtOH STY + (AcOEt STY × 46.07/88.10).

Example 6

A mixture of carbon monoxide (63.4 vol %), $H_2$ (31.6 vol %), and methyl ethanoate (5.0 vol %) was passed over T-4489 at 190° C., with a pressure of 5 MPa and a GHSV of 5400 $h^{-1}$ for 18 h. The observed conversion of methyl ethanoate was 92.1%; the observed selectivity (to ethanol and the ethyl portion of ethyl ethanoate) was 99.8%; and the observed productivity (defined as kilograms of ethanol plus kilograms of the ethyl portion of ethyl ethanoate produced per kilogram of catalyst per hour) was 0.36 kg/$kg_{cat}$/h.

Comparative Example H

A mixture of nitrogen (63.4 vol %), $H_2$ (31.6 vol %), and methyl ethanoate (5.0 vol %) was passed over T-4489 at 190° C., with a pressure of 5 MPa and a GHSV of 5400 for 18 h. The observed conversion of methyl ethanoate was 67.1%; the observed selectivity (to ethanol and the ethyl portion of ethyl ethanoate) was 99.8%; and the observed productivity (defined as kilograms of ethanol plus kilograms of the ethyl portion of ethyl ethanoate produced per kilogram of catalyst per hour) was 0.26 kg/$kg_{cat}$/h.

Comparative Example I

A mixture of carbon monoxide (63.4 vol %), $H_2$ (31.6 vol %), and methyl ethanoate (5.0 vol %) was passed over T-2130 at 190° C., with a pressure of 5 MPa and a GHSV of 5400 $h^{-1}$ for 18 h. The observed conversion of methyl ethanoate was 9.4%; the observed selectivity (to ethanol and the ethyl portion of ethyl ethanoate) was 99.9%; and the observed productivity (defined as kilograms of ethanol plus kilograms of the ethyl portion of ethyl ethanoate produced per kilogram of catalyst per hour) was 0.05 kg/$kg_{cat}$/h.

Comparative Example J

A mixture of nitrogen (63.4 vol %), $H_2$ (31.6 vol %), and methyl ethanoate (5.0 vol %) was passed over T-2130 at 190° C., with a pressure of 5 MPa and a GHSV of 5400 $h^{-1}$ for 18 h. The observed conversion of methyl ethanoate was 28.1%; the observed selectivity (to ethanol and the ethyl portion of ethyl ethanoate) was 99.8%; and the observed productivity (defined as kilograms of ethanol plus kilograms of the ethyl portion of ethyl ethanoate produced per kilogram of catalyst per hour) was 0.14 kg/$kg_{cat}$/h.

The results for Example 6 and comparative Examples H to J show that the hydrogenation rate was increased by the presence of carbon monoxide for the hydrogenation catalyst containing copper and manganese (T-4489), but was decreased by the presence of carbon monoxide for the on-manganese containing catalyst (T-2130).

The invention claimed is:

1. A process for the preparation of alcohol(s) from alkyl ester(s) which comprises bringing hydrogen, carbon monoxide and at least one alkyl ester into contact with a hydrogenation catalyst comprising copper and manganese in a reaction zone to produce at least one alcohol, wherein the molar ratio of hydrogen to carbon monoxide in the reaction zone is in the range of from 100:1 to 1:10.

2. A process according to claim 1, wherein the molar ratio of hydrogen to carbon monoxide in the reaction zone is in the range of from 50:1 to 1:2.

3. A process according to claim 1, wherein the hydrogen and carbon monoxide are sourced from a process generating synthesis gas.

4. A process according to claim 3, wherein the synthesis gas has been subjected to a process to remove carbon dioxide.

5. A process according to claim 1, wherein the alkyl ester(s) is selected from methyl ethanoate, ethyl ethanoate, methyl propanoate, ethyl propanoate, propyl butanoate, butyl pentanoate, and mixtures thereof.

6. A process according to claim 1, wherein the molar ratio of hydrogen to alkyl ester in the reaction zone is greater than 1.5:1.

7. A process according to claim 1, wherein the molar ratio of hydrogen to alkyl ester in the reaction zone is less than 100:1.

8. A process according to claim 1, wherein the alkyl ester(s) in the reaction zone is in the gas phase.

9. A process according to claim 1, wherein the hydrogenation catalyst comprising copper and manganese comprises:
   (a) a copper component;
   (b) a manganese component; and
   (c) at least one additional component selected from metal oxide, silicon oxide, clay, carbon and graphite.

10. A process according to claim 9, wherein the hydrogenation catalyst comprising copper and manganese contains a copper component and a manganese component supported on a support material selected from carbon, silica, titania, clays, alumina, zinc oxide, zirconia, and mixtures thereof.

11. A process according to claim 1, wherein the hydrogenation catalyst comprising copper and manganese is a manganese-containing copper chromite catalyst.

12. A process according to claim 1, wherein the hydrogenation catalyst comprising copper and manganese is a mixed metal oxide catalyst containing copper oxide, manganese and at least one other metal oxide.

13. A process according to claim 1, wherein the hydrogenation catalyst comprising copper and manganese contains at least 0.1 wt % manganese.

14. A process according to claim 1, wherein the hydrogenation catalyst comprising copper and manganese contains at least 5 wt % copper.

* * * * *